(12) United States Patent
Buyuktimkin et al.

(10) Patent No.: US 11,229,617 B2
(45) Date of Patent: Jan. 25, 2022

(54) TOPICAL ANTI-INFLAMMATORY COMPOSITIONS

(71) Applicant: Achelios Therapeutics, Inc., Durham, NC (US)

(72) Inventors: Servet Buyuktimkin, San Diego, CA (US); Nadir Buyuktimkin, San Diego, CA (US); James L. Yeager, Lake Forest, IL (US)

(73) Assignee: ACHELIOS THERAPEUTICS, INC., Durham, NC (US)

( * ) Notice: Subject to any disclaimer, the term of this patent is extended or adjusted under 35 U.S.C. 154(b) by 42 days.

(21) Appl. No.: 16/887,390

(22) Filed: May 29, 2020

(65) Prior Publication Data

US 2020/0360325 A1  Nov. 19, 2020

Related U.S. Application Data

(63) Continuation of application No. 16/332,124, filed as application No. PCT/US2017/051560 on Sep. 14, 2017, now abandoned.

(60) Provisional application No. 62/395,804, filed on Sep. 16, 2016.

(51) Int. Cl.
| | |
|---|---|
| *A61K 31/196* | (2006.01) |
| *A61K 9/00* | (2006.01) |
| *A61K 31/192* | (2006.01) |
| *A61K 47/10* | (2017.01) |
| *A61K 47/12* | (2006.01) |
| *A61K 47/20* | (2006.01) |
| *A61K 47/36* | (2006.01) |

(52) U.S. Cl.
CPC .......... *A61K 31/196* (2013.01); *A61K 9/0014* (2013.01); *A61K 31/192* (2013.01); *A61K 47/10* (2013.01); *A61K 47/12* (2013.01); *A61K 47/20* (2013.01); *A61K 47/36* (2013.01)

(58) Field of Classification Search
CPC .... A61K 31/192; A61K 31/196; A61K 47/10; A61K 47/12; A61K 47/14; A61K 47/20; A61K 47/36; A61K 9/0014; A61P 29/00
See application file for complete search history.

*Primary Examiner* — Savitha M Rao
(74) *Attorney, Agent, or Firm* — Olson & Cepuritis, Ltd.

(57) ABSTRACT

A topical composition includes a non-steroidal anti-inflammatory drug (NSAID) in an aqueous carrier system which contains a cationic galactomannan gum. The carrier system includes, in addition to water and the cationic galactomannan gum, a lactate ester of a $C_2$ to $C_{16}$ saturated aliphatic alcohol, a monoprotic arylalkanoic acid (pKa 3.8 to 5), a solubility enhancer, and a $C_2$ to $C_8$ saturated aliphatic alcohol.

17 Claims, 5 Drawing Sheets

TOPICAL ANTI-INFLAMMATORY COMPOSITIONS

CROSS-REFERENCE TO RELATED APPLICATION

This application is a continuation of U.S. Ser. No. 16/332,124, filed on Mar. 11, 2019, which is a 371 of PCT/US2017/051560, filed on Sep. 14, 2017, which claims benefit of U.S. Provisional Application No. 62/395,804, filed on Sep. 16, 2016, each of which is incorporated herein by reference in its entirety.

FIELD OF INVENTION

This invention relates to topical compositions. More particularly, this invention relates to topical anti-inflammatory compositions containing non-steroidal anti-inflammatory drugs (NSAIDS).

BACKGROUND OF THE INVENTION

Anti-inflammatory drugs are medicaments used to ameliorate muscle pains, sprains, strains, as well as arthritis pains. These drugs can be administered orally (e.g., tablets, liquids, capsules), injected, or applied to the skin. When applied to the skin, such medicaments are referred to as topical anti-inflammatory painkillers. One such group of medicaments, by reason of their chemical structure are usually referred to as topical non-steroidal anti-inflammatory drugs or topical NSAIDS.

When NSAIDS are taken orally they work by inhibiting the cyclo-oxygenate (cox) enzymes which make prostaglandins that are involved in causing pain and inflammation at injured body sites. A reduction in prostaglandins, in turn, results in reduction of pain. Topical NSAIDS function in the same manner, but instead of a systemic effect, the pain relief is provided in the region or area to which the topical preparation has been applied. Upon topical application, the NSAIDS are first absorbed into the skin and then move deeper into an inflamed region of the body and relieve pain and reduce swelling of the affected joints and tissues. As compared to any route of systemic administration, topically applied NSAIDS introduce into the body a relatively low amount of the drug and thus reduce the likelihood of adverse side effects. Yet currently available topical NSAID preparations are relatively slow in releasing the drug into the affected area.

It has now been found, however, that the rate of release of NSAIDS from topical gels can be enhanced by the use of specific aqueous carrier systems for NSAIDS.

SUMMARY OF THE INVENTION

An arylalkanoic acid non-steroidal anti-inflammatory drug (NSAID) in an aqueous carrier that includes a cationic galactomannan gum system provides a topical composition that enhances skin penetration of the NSAID and is suitable for treating inflammation, mild to moderate pain, and fever.

The arylalkanoic acid can be an arylethanoic acid or its pharmaceutically acceptable salt form, e.g., diclofenac, diclofenac sodium, and the like, or an arylpropanoic acid or its pharmaceutically acceptable salt form, e.g., naproxen, naproxen sodium, ketoprofen, and the like.

The aqueous carrier system includes, in addition to water, a lactate ester of a $C_2$ to $C_{16}$ saturated aliphatic alcohol, a monoprotic organic acid having a pKa value in the range of about 3.8 to about 5, a $C_2$ to $C_8$ saturated aliphatic alcohol, a solubility enhancer, and a cationic galactomannan gum.

The topical composition contains the arylalkanoic acid in an amount in the range of about 0.5 to about 7, preferably about 0.75 to about 5, percent by weight, based on the total weight of the composition.

DESCRIPTION OF PREFERRED EMBODIMENTS

Figure 1:
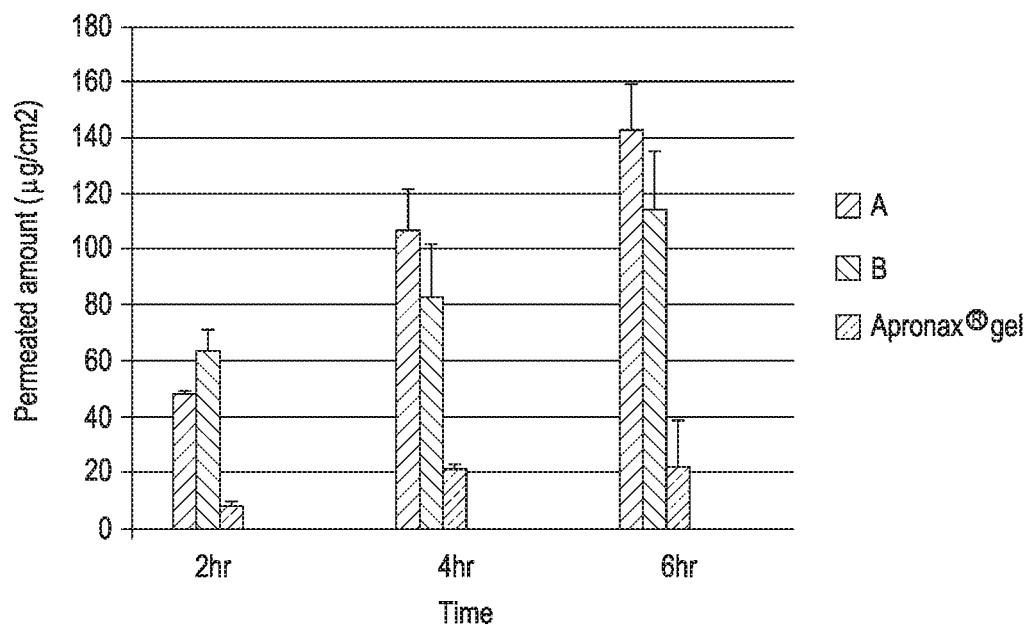
FIG. 1 is a histogram showing skin permeation of naproxen, from topical compositions over a six-hour time period.

The topical compositions embodying the present invention are relatively low viscosity gels having a pH value in the range of about 3 to about 5.5. These gels can be readily dispersed and applied to body regions to be treated in an effective amount without causing irritation, providing enhanced delivery of the NSAID to the affected region for the treatment of inflammation and pain.

Suitable NSAIDS are the arylalkanoic acids, including the pharmaceutically acceptable salts thereof, such as arylethanoic (arylacetic) acids, arylpropanoic acids, and their salts. Illustrative arylethanoic acids are diclofenac, diclofenac sodium, diclofenac potassium, diclofenac diethylamine, diclofenac epolamine, indomethacin sodium, indomethacin meglumine, ketorolac tromethamine, tolmetin sodium, etodolac, sulindac, nabumetone, and the like. Illustrative arylpropanoic acids are naproxen, naproxen sodium, naproxen piperazine, ketoprofen, ketoprofen sodium, ketoprofen lysine, ibuprofen, ibuprofen sodium, ibuprofen lysine, fenoprofen, fenoprofen calcium, flurbiprofen and the like.

The topical compositions contain an arylalkanoic acid in an amount in the range of about 0.5 to about 7, preferably about 0.75 to about 5, percent by weight, based on the total weight of the composition.

Preferably, the present topical anti-inflammatory compositions also include a photostabilizer which absorbs UVA and UVB ultraviolet radiation, i.e., ultraviolet radiation in the 280 to 400 nanometer wavelength region. Suitable photostabilizers for the present topical compositions are the benzophenones such as oxybenzone (benzophenone-3), sulisobenzone (benzophenone-4), and the like, the dibenzoylmethane derivatives such as avobenzone [1-(4-methoxyphenyl)-3-(4-tert-butylphenyl)propane-1,3-dione)], and the like, the cinnmamate derivatives such as ethylhexyl methoxycinnamate, isoamyl methoxycinnamate, and the like, the acrylates such as octocrylene (2-ethylhexyl-2-cyano-3,3-diphenylacrylate, ethyl-2-cyano-3,3-diphenylacrylate), and the like, as well as mixtures of the foregoing.

In the present topical compositions the photostabilizer preferably is present in an amount in the range of about 0.5 to about 2.5 percent by weight, more preferably about 0.75 to about 1.5 percent by weight, based on the total weight of the composition.

The photostabilizers may be used with or without a solubilizer such as phenethyl benzoate, dipropylene glycol dibenzoate (DiPG-dibenzoate), 2-(2-ethoxyethoxy)ethanol (Transcutol), and the like. Levulinic acid, if present, can also aid in solubilization of a photostabilizer such as oxybenzone.

The present topical anti-inflammatory compositions can also contain crystallization inhibitors such as polymeric precipitation inhibitors, e.g., low molecular weight polyvinylpyrrolidone, hydroxymethyl cellulose, polyethylene glycol poloxamers, and the like, polysorbate surfactants, e.g., polyoxyethylene (20) sorbitan monolaurate, and the like, sugar alcohols such as sorbitol, and the like.

In the present topical compositions the photostabilizer can be present preferably in an amount in the range of about 0.25 to about 2 percent by weight, based on the total weight of the composition, more preferably about 0.5 to about 1.5 percent by weight, based on the total weight of the composition.

Illustrative lactate esters of a $C_2$ to $C_{16}$ saturated aliphatic alcohol are ethyl lactate, n-butyl lactate, isoamyl lactate, 1,2-ethylhexyl lactate, lauryl lactate, myristyl lactate, cetyl lactate, and the like. A preferred lactate ester is lauryl lactate.

The lactate ester content of the present compositions is in the range of about 0.5 to about 5, preferably about 1 to about 3, percent by weight, based on the total weight of the composition.

Suitable monoprotic organic acids are those having a pKa value in the range of about 3.8 to about 5, preferably about 4.6 to about 4.8. Illustrative such acids are lactic acid (pKa 3.9), hydroxymethyl-butyric acid (pKa 4.55), levulinic acid (pKa 4.6), acetic acid (pKa 4.8), hexanoic (caproic) acid (pKa 4.88), and the like.

The monoprotic organic acid content of the present compositions is in the range of about 0.5 to about 5, preferably about 0.75 to about 4, percent by weight, based on the total weight of the composition.

Suitable $C_2$ to $C_8$ saturated aliphatic alcohols can be monohydric as well as dihydric. Illustrative $C_2$ to $C_8$ monohydric saturated aliphatic alcohols are ethanol, propanol, isopropanol, n-butanol, the hexanols, and the like. Illustrative $C_2$ to $C_8$ dihydric saturated aliphatic alcohols are ethylene glycol, propylene glycol, butylene glycol, hexylene glycol, and the like.

The $C_2$ to $C_8$ saturated aliphatic alcohol content of the present compositions is in the range of about 35 to about 60, preferably about 40 to about 55, percent by weight, based on the total weight of the composition. The present compositions can contain only a monohydric $C_2$ to $C_8$ saturated aliphatic alcohol, only a dihydric $C_2$ to $C_8$ saturated aliphatic alcohol, or a mixture of monohydric and dihydric $C_2$ to $C_8$ saturated aliphatic alcohols. Particularly preferred is a mixture of ethanol and propylene glycol is a respective weight ratio in the range of about 3.5:1 to about 4.5:1.

Suitable solubility enhancers are the monoglycerides such as glycerol monooleate, glycerol monolaurate, glycerol monolinoleate, mixtures thereof, and the like. Preferred solubility enhancer is glycerol monolaurate. The solubility enhancer content of the present compositions is in the range of about 0.5 to about 5, preferably about 2 to about 4, percent by weight, based on the total weight of the composition.

Galactomannan gums are polysaccharides having a mannose backbone and galactose side groups such as fenugreek gum (mannose:galactose~1:1), guar gum (mannose:galactose~2:1), tara gum (mannose:galactose~3:1) and locust bean gum (mannose:galactose~4:1). Suitable for use in the present compositions are cationic galactomannan gums, i.e., galactomannan gums containing cationic groups and/or groups which can be ionized to cationic groups. Preferred cationic groups are primary, secondary, tertiary and/or quaternary amine groups.

Particularly preferred are cationic guar gums with hydroxypropyl-trimethylammonium groups and salts thereof such as guar gum, 2-hydroxy-3-(trimethyl-ammonium) propyl ether chloride, and the like, commercially available under the designation Jaguar C162 from various sources such as Rhodia Operations, 93306 Aubervilliers Cedex, France, Solvay USA Inc., Cranbury, N.J., USA.

Suitable cationic guar gums are also described in U.S. Pat. No. 4,031,307 to DeMartino et al., U.S. Pat. No. 5,536,825 to Yeh et al., and U.S. Pat. No. 8,501,932 to Baldaro et al.

The cationic galactomannan gum content in the present compositions is in the range of about 1 to about 5, preferably about 1.5 to about 4, percent by weight, based on the total weight of the composition.

The topical compositions described herein can be prepared in the following manner.

A cationic guar gum is dispersed in water with agitation at room temperature. In a separate vessel the NSAID is combined with a lactate ester, the monoprotic organic acid, the $C_2$ to $C_8$ saturated aliphatic alcohol, and a solubility enhancer. An aliquot of water is added after the monoprotic organic acid has been dissolved, and the resulting solution is agitated thoroughly. The photostabilizer, if desired, is added concurrently.

Thereafter the solution is transferred quantitatively to the aqueous dispersion of the cationic guar gum with vigorous agitation for a time period of at least two hours until a substantially homogeneous gel is achieved. The obtained gel is then left standing before packaging for a time period sufficient for entrained air bubbles to disperse.

Skin permeation studies of illustrative topical compositions embodying the invention were performed using dermatomed human male cadaver skin pieces from the back (Science Care, Aurora, CO; 250 micrometers thick), Franz cells (3.65 ml volume, 0.55 cm² surface area) at 35° C. using heating/stirring blocks. Receptor compartment contained saline with sodium azide (pH 5.5).

Four or five replicates (25 ml and 25 mg control) were prepared for each sample. Sampling volume was 300 ml. Fresh buffer was replaced after each sample removal. The samples were assayed using high performance liquid chromatography (HPLC).

For naproxen the control was Apronax® gel (5.5% naproxen sodium) or Flanax® gel (5.5% naproxen sodium), Bayer de Mexico S.A., Lerma, Mexico.

For diclofenac the control was Voltaren® gel (1% diclofenac sodium), Novartis Pharma Productions GmbH, Wehr, Germany.

For ibuprofen the control was Ibutop™ Schmerzgel gel (5% ibuprofen), Axicorp Pharma GmbH, Friedrichsdorf, Germany, or Ibuleve™, DDD Limited, 94 Rickmansworth Road, Watford, Herts, U.K.

Results of the skin permeation studies are presented below.

Topical compositions shown in Table 1, below, and containing about 2.5 percent by weight naproxen or sodium salt of naproxen were compared with Apronax® gel containing about 5.5 percent by weight naproxen sodium. Skin permeation results are presented in Table 2, below, and in FIG. 1.

TABLE 1

Naproxen Compositions

| Ingredient | Composition A, wt.-% | Composition B, wt.-% | Apronax ® Gel, wt.-% |
| --- | --- | --- | --- |
| Naproxen sodium | 2.5 | | 5.5 |
| Naproxen | | 2.5 | |
| Propylene glycol | 10 | 10 | |
| Lauryl lactate | 3 | 3 | |
| Lactic acid | 1.5 | 1.5 | |
| Cationic Guar Gum[1] | 2 | 2 | |
| Glycerol monolaurate | 3 | 3 | |
| Ethanol, absolute | 38 | 38 | |
| Water | 40 | 40 | |
| TOTAL | 100 | 100 | |

[1]Jaguar C162; CAS No. 71329-50-5; contains 11.5% w/w water

TABLE 2

Skin Permeation Data for Naproxen

Cumulative Permeated Amount, $\mu g/cm^2$

| | Composition A | | Composition B | | Apronax ® Gel | |
| --- | --- | --- | --- | --- | --- | --- |
| Time, Hrs. | Amt. | ±SD | Amt. | ±SD | Amt. | ±SD |
| 2 | 48.7 | 0.3 | 63.6 | 7.5 | 8.5 | 1.3 |
| 4 | 107.4 | 14.0 | 83.5 | 18.3 | 21.6 | 1.0 |
| 6 | 143.1 | 16.5 | 114.8 | 20.6 | 22.3 | 17.2 |

The above skin permeation data show that the present compositions, containing a relatively lower concentration of naproxen provided more skin penetration of naproxen that a commercially available naproxen sodium gel having a relatively higher naproxen concentration. The data further show that the skin penetration of naproxen sodium and naproxen was about the same.

Figure 2:
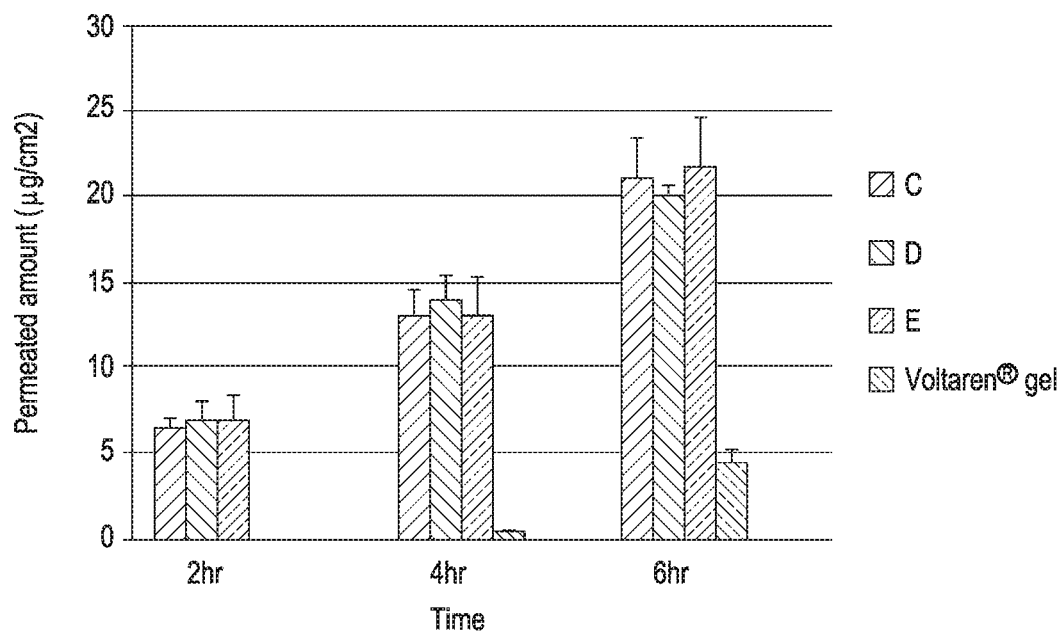
FIG. 2 is a histogram showing skin permeation of diclofenac from topical compositions over a six-hour time period.

Topical compositions shown in Table 3, below, and containing about 1 percent by weight of diclofenac, diclofenac sodium, or diclofenac diethylamine were evaluated for skin permeation and compared with Voltaren® Gel performance. The observed results are presented in Table 4, below, and in FIG. 2.

TABLE 3

Diclofenac Compositions

| Ingredient | Composition C, wt.-% | Composition D, wt.-% | Composition E, wt.-% |
| --- | --- | --- | --- |
| Diclofenac sodium | 1 | | |
| Diclofenac | | 1 | |
| Diclofenac diethylamine | | | 1 |
| Propylene glycol | 10 | 10 | 10 |
| Lauryl lactate | 3 | 3 | 3 |
| Lactic acid | 1.5 | 1.5 | 1.5 |
| Cationic guar gum[1] | 2 | 2 | 2 |
| Glycerol monolaurate | 3 | 3 | 3 |
| Ethanol, absolute | 39.5 | 39.5 | 39.5 |
| Water, deionized | 40 | 40 | 40 |
| TOTAL | 100 | 100 | 100 |

[1]Jaguar C162; CAS No. 71329-50-5; contains 11.5% w/w water

TABLE 4

Skin Permeation Data for Diclofenac

Cumulative Permeated Amount, $\mu g/cm^2$

| | Composition C | | Composition D | | Composition E | | Voltaren ® Gel | |
| --- | --- | --- | --- | --- | --- | --- | --- | --- |
| Time, Hrs. | Amt. | ±SD | Amt. | ±SD | Amt. | ±SD | Amt. | ±SD |
| 2 | 6.6 | 0.6 | 7.0 | 1.1 | 7.0 | 1.5 | 0.0 | 0 |
| 4 | 13.1 | 1.4 | 14.0 | 1.5 | 13.1 | 2.2 | 0.5 | |
| 6 | 21.1 | 2.3 | 20.0 | 0.7 | 21.7 | 2.9 | 4.5 | 0.6 |

The above skin penetration data show significant enhancement of diclofenac delivery by the topical compositions containing a cationic guar gum as compared to Voltaren® gel, a commercially available product containing about the same amount of diclofenac.

TABLE 5

Ibuprofen Compositions

| Ingredient | Composition, wt.-% | | | | | | | |
|---|---|---|---|---|---|---|---|---|
| | F | G | H | I | J[1] | K[1] | L | Ibuleve ™ |
| Ibuprofen | 5 | 5 | 5 | 5 | 5 | 5 | 5 | 5 |
| Isopropyl myristate | | | | | 3 | 3 | | |
| Diisopropyl adipate | | | | | | | 3 | |
| Lauryl lactate | 3 | 3 | 3 | 3 | 3 | 3 | 3 | |
| Lactic acid | 1.5 | 1.5 | 2.5 | | 1.5 | 2.5 | 1.5 | |
| Levulinic acid | | | | 2.5 | | | | |
| Cationic guar gum[2] | 2 | 2 | 2 | 2 | 2 | 2 | 2 | |
| Glycerol monolaurate | 3 | 3 | 3 | 3 | 3 | 3 | 3 | |
| Ethanol, absolute | 35.5 | 45.5 | 44.5 | 44.5 | 42.5 | 41.5 | 42.5 | |
| Propylene glycol | 10 | | | | | | | |
| Water, deionized | 40 | 40 | 40 | 40 | 40 | 40 | 40 | |
| TOTAL | 100 | 100 | 100 | 100 | 100 | 100 | 100 | |

Figure 3:
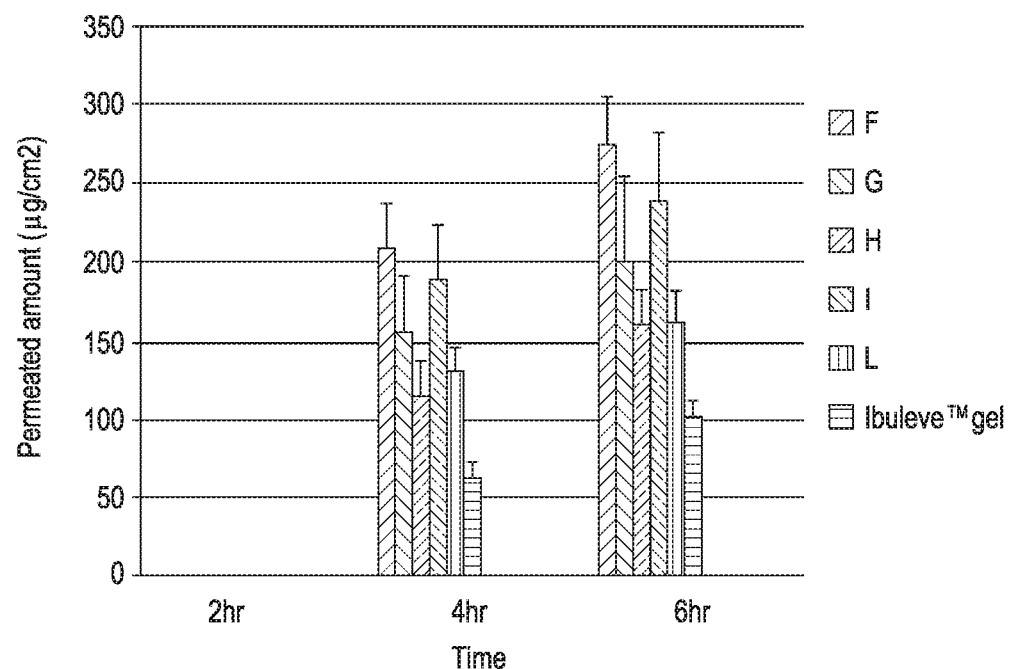
FIG. 3 is a histogram showing skin permeation of ibuprofen from topical compositions over a six-hour time period.

[1]Compositions not physically stable
[2]Jaguar C162; CAS No. 71329-50-5; contains 11.5% w/w water The compositions listed in Table 5 and containing about 5 percent by weight of ibuprofen were evaluated for skin permeation performance and compared to Ibuleve™ gel. The observed results are presented in Table 6, below, and in FIG. 3.

TABLE 6

Skin Permeation Data for Ibuprofen

| | Cumulative Permeated Amount, µg/cm² | | | | | | | | | | | |
|---|---|---|---|---|---|---|---|---|---|---|---|---|
| Time, | F | | G | | H | | I | | L | | Ibuleve ™ gel | |
| hrs. | Amt. | ±SD | Amt. | ±SD | Amt. | ±SD | Amt. | ±SD | Amt. | ±SD | Amt. | ±SD |
| 2 | 0 | 0 | 0 | 0 | 0 | 0 | 0 | 0 | 0 | 0 | 0 | 0 |
| 4 | 209.2 | 27.6 | 156.1 | 35.8 | 115.6 | 22.1 | 189.2 | 34.4 | 131.1 | 15.6 | 63.2 | 9.0 |
| 6 | 273.3 | 30.8 | 200.0 | 53.7 | 161.0 | 21.4 | 239.1 | 42.0 | 162.2 | 20.1 | 102.2 | 8.2 |

The above skin permeation data show significant enhancement of ibuprofen delivery by the topical compositions containing a cationic guar gum as compared to Ibutop™ gel, a commercial product containing about the same amount of ibuprofen.

Tables 7 and 8, below, illustrate the effect of cationic guar gum on skin permeation.

TABLE 7

Ibuprofen Compositions

| Ingredient | Composition, wt.-% | | |
|---|---|---|---|
| | M | N | Ibutop ™ |
| Ibuprofen | 5 | 5 | 5 |
| Lauryl lactate | 3 | 3 | |
| Lactic acid | 1.5 | 1.5 | |
| Cationic guar gum[3] | 0 | 2 | |

TABLE 7-continued

Ibuprofen Compositions

| Ingredient | Composition, wt.-% | | |
|---|---|---|---|
| | M | N | Ibutop ™ |
| Glycerol monolaurate | 3 | 3 | |
| Propylene glycol | 10 | 10 | |
| Ethanol | 37.5 | 37.5 | |
| Water | 40 | 40 | |
| TOTAL | 100 | 100 | |

[3]Jaguar C162; CAS No. 71329-50-5; contains 11.5% w/w water

The compositions shown in Table 7 were applied to cadaver skin from the back of a 68-year old male, weighing 170 pounds, in a Franz cell skin permeation study. The results are shown in Table 8, below.

TABLE 8

Skin Permeation Data

| Time, Hrs. | Cumulative Permeated Amount, μg/cm² | | | | | |
|---|---|---|---|---|---|---|
| | M | | N | | Ibutop ™ | |
| | Amt. | ±SD | Amt. | ±SD | Amt. | ±SD |
| 2 | 21.16 | 7.70 | 30.81 | 2.86 | 4.92 | 1.24 |
| 4 | 45.05 | 16.30 | 68.16 | 7.87 | 12.63 | 1.31 |
| 6 | 77.81 | 25.86 | 133.40 | 3.70 | 25.28 | 5.24 |

The foregoing data indicate that stain permeation is enhanced by the presence of the cationic guar gum.

The use of crystallization inhibitors in the present naproxen compositions is illustrated in Tables 9-12, below.

TABLE 9

Naproxen Salt Compositions With Crystallization Inhibitors

| | O MRL-2014-Np-45 | P[4] MRL-2014-Np-51 | Q MRL-2015-Np-52 | R MRL-2015-Np-53 | S MRL-2015-Np-54 | T MRL-2015-Np-55 | U Flanax ™ |
|---|---|---|---|---|---|---|---|
| Naproxen Na | 1.5 | 1.5 | 1.5 | 1.5 | 1.5 | 1.5 | 5.5 |
| Propylene glycol | 10 | 10 | 10 | 10 | 10 | 10 | |
| Lauryl lactate | 3 | 3 | 3 | 3 | 3 | 3 | |
| Lactic acid | 1.5 | 1.5 | 1.5 | 1.5 | 1.5 | 1.5 | |
| Cationic guar gum[5] | 2 | 2 | 2 | 2 | 2 | 2 | |
| Glycerol monolaurate | 3 | 3 | 3 | 3 | 3 | 3 | |
| Ethanol | 44 | 44 | 44 | 44 | 43 | 43 | |
| Water | 35 | 35 | 35 | 35 | 35 | 35 | |
| Polyvinyl acetate 80% | | 1 | | | | | |
| Poloxamer[6] | | | 1 | | | | |
| Polyvinyl pyrrolidone[7] | | | | 1 | | | |
| Polyoxyethylene (20) sorbitan monolaurate[8] | | | | | 1 | | |
| Sorbitol 70% | | | | | | 1 | |
| TOTAL | 100 | 101 | 101 | 101 | 100 | 100 | |

[4]Not a clear gel
[5]Jaguar C162; CAS No. 71329-50-5; contains 11.5% w/w water
[6]Pluronic 127
[7]Kollidon 12
[8]Tween 20

Figure 4:
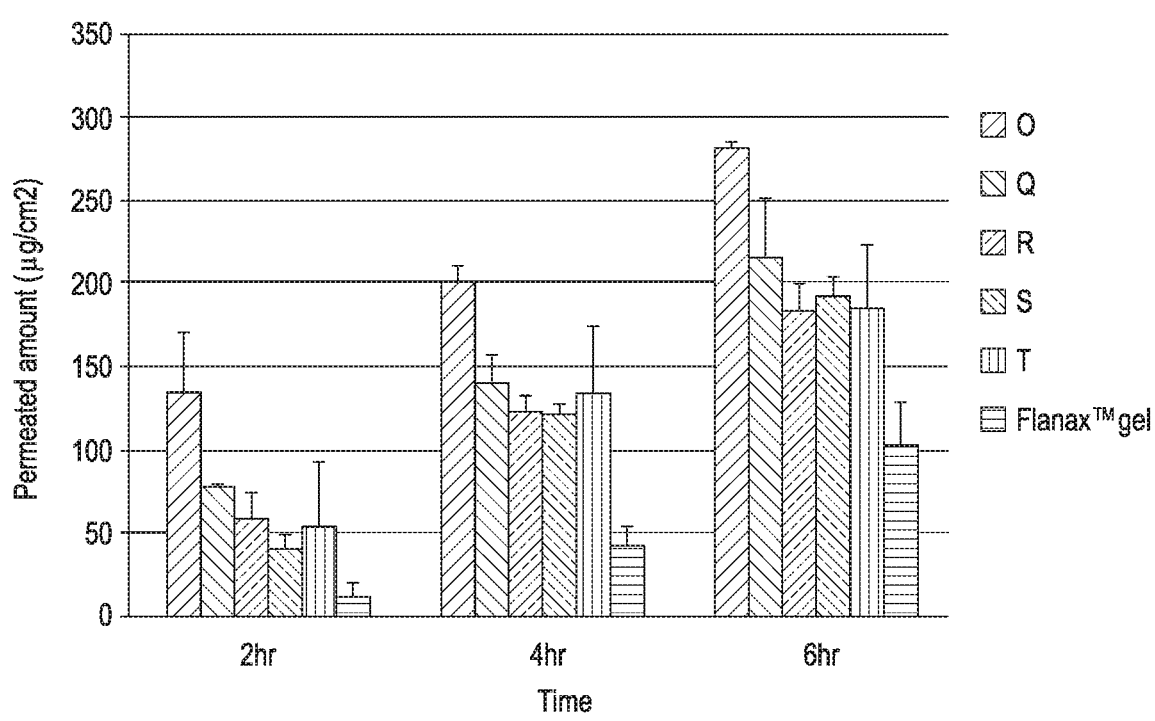
FIG. 4 is a histogram showing skin permeation of topical naproxen salt compositions over a six-hour time period.

The compositions shown in Table 9 were applied to cadaver skin from the back of a 64-year old male, weighing 250 pounds, in a Franz cell skin permeation study. The results are shown in Table 10, below, and in FIG. 4.

TABLE 10

Skin Permeation Data for Naproxen Salt Compositions With Crystallization Inhibitors

| Time, hrs. | Cumulative Permeated Amount, μg/cm² | | | | | | | | | | | |
|---|---|---|---|---|---|---|---|---|---|---|---|---|
| | O | | Q | | R | | S | | T | | Flanax ™ | |
| | Amt. | ±SD | Amt. | ±SD | Amt. | ±SD | Amt. | ±SD | Amt. | ±SD | Amt. | ±SD |
| 2 | 135.8 | 33.4 | 79.0 | 0.8 | 60.3 | 14.4 | 41.9 | 7.5 | 54.7 | 11.4 | 13.9 | 6.6 |
| 4 | 202.0 | 9.5 | 141.7 | 16.7 | 123.6 | 10.0 | 122.9 | 4.7 | 135.4 | 43.8 | 44.2 | 12.1 |
| 6 | 283.3 | 3.0 | 216.9 | 33.8 | 184.1 | 16.3 | 193.5 | 11.0 | 186.1 | 100.9 | 103.3 | 25.2 |

TABLE 11

Naproxen Free Acid Compositions With Crystallization Inhibitors

| | V MRL-2014-Np-46 | W[9] MRL-2014-Np-56 | X MRL-2015-Np-57 | Y MRL-2015-Np-58 | Z MRL-2015-Np-59 | AA MRL-2015-Np-60 | Flanax ™ |
|---|---|---|---|---|---|---|---|
| Naproxen Na | | | | | | | 5.5 |
| Naproxen | 1.5 | 1.5 | 1.5 | 1.5 | 1.5 | 1.5 | |
| Propylene glycol | 10 | 10 | 10 | 10 | 10 | 10 | |
| Lauryl lactate | 3 | 3 | 3 | 3 | 3 | 3 | |
| Lactic acid | 1.5 | 1.5 | 1.5 | 1.5 | 1.5 | 1.5 | |
| Cationic guar gum[10] | 2 | 2 | 2 | 2 | 2 | 2 | |
| Glycerol monolaurate | 3 | 3 | 3 | 3 | 3 | 3 | |
| Ethanol | 44 | 43 | 43 | 43 | 43 | 43 | |
| Water | 35 | 35 | 35 | 35 | 35 | 35 | |
| Polyvinyl acetate 80% | | 1 | | | | | |
| Poloxamer[11] | | | 1 | | | | |
| Polyvinyl pyrrolidone[12] | | | | 1 | | | |
| Polyoxyethylene (20) sorbitan monolaurate[13] | | | | | 1 | | |
| Sorbitol 70% | | | | | | 1 | |
| TOTAL | 100 | 100 | 100 | 100 | 100 | 100 | |

[9]Not a clear gel
[10]Jaguar C162; CAS No. 71329-50-5; contains 11.5% w/w water
[11]Pluronic 127
[12]Kollidon 12
[13]Tween 20

Figure 5:
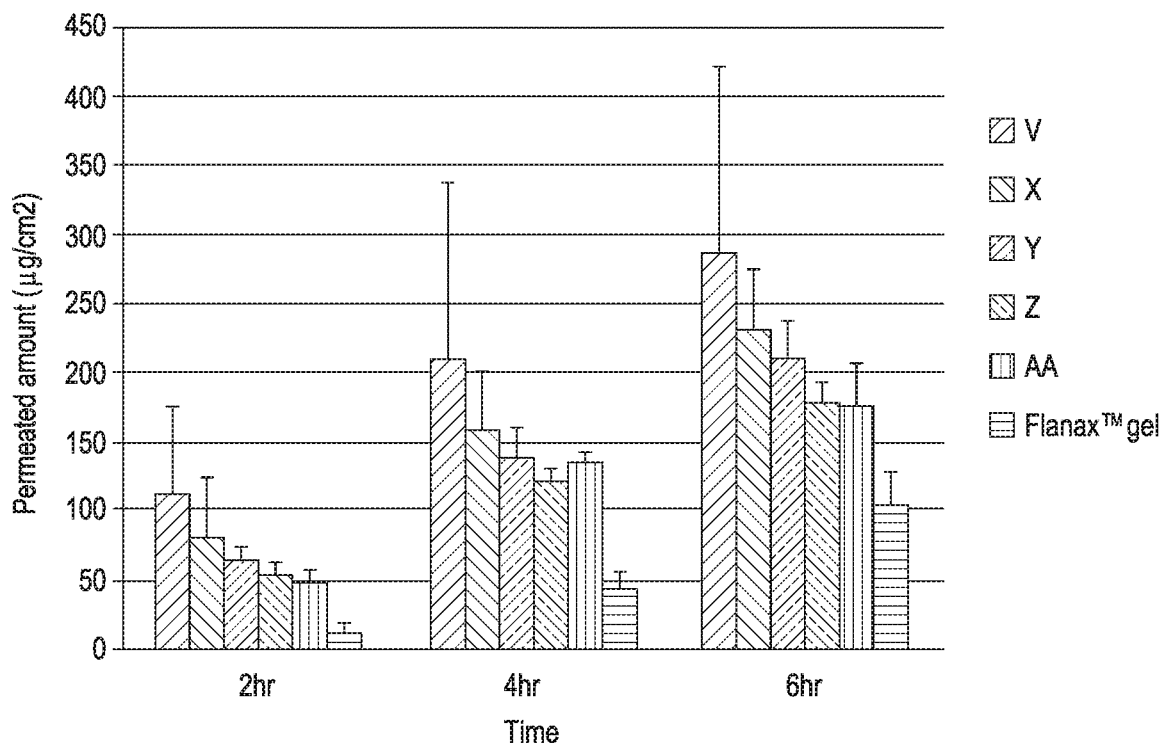
FIG. 5 is a histogram showing skin permeation of topical naproxen free acid compositions over a six-hour time period.

The compositions shown in Table 11 were applied to cadaver skin from the back of a 64-year old male, weighing 250 pounds, in a Franz cell skin permeation study. The results are shown in Table 12, below, and in FIG. 5.

TABLE 12

Skin Permeation Data for Naproxen Free Acid
Compositions With Crystallization Inhibitors Cumulative Permeated Amount, $\mu g/cm^2$

| Time, hrs. | V Amt. | ±SD | X Amt. | ±SD | Y Amt. | ±SD | Z Amt. | ±SD | AA Amt. | ±SD | Flanax™ Amt. | ±SD |
|---|---|---|---|---|---|---|---|---|---|---|---|---|
| 2 | 114.4 | 62.6 | 82.4 | 51.2 | 66.9 | 8.5 | 56.5 | 8.2 | 51.1 | 7.6 | 13.9 | 6.6 |
| 4 | 210.3 | 127.6 | 158.9 | 58.6 | 137.8 | 23.1 | 122.8 | 6.2 | 136.7 | 4.6 | 44.2 | 12.1 |
| 6 | 285.6 | 131.9 | 230.3 | 172.6 | 208.4 | 29.1 | 177.9 | 12.9 | 175.5 | 30.0 | 103.3 | 25.2 |

Figure 6:
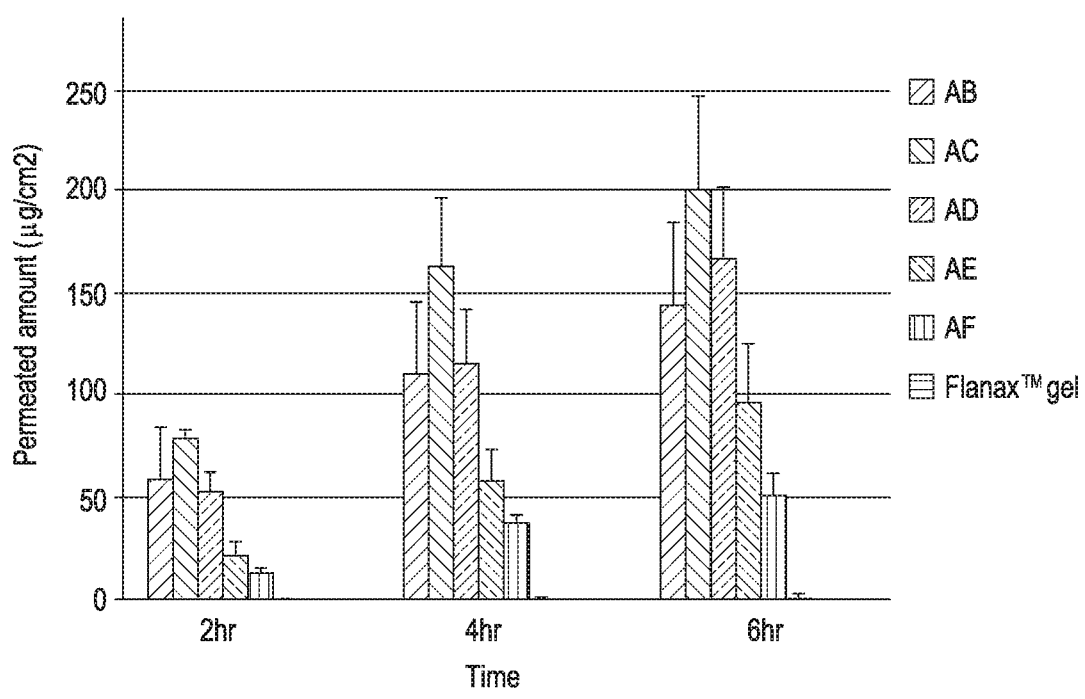
FIG. 6 is a histogram showing skin permeation of topical naproxen salt compositions having varying amounts of lactic acid over a six-hour time period.
Figure 7:
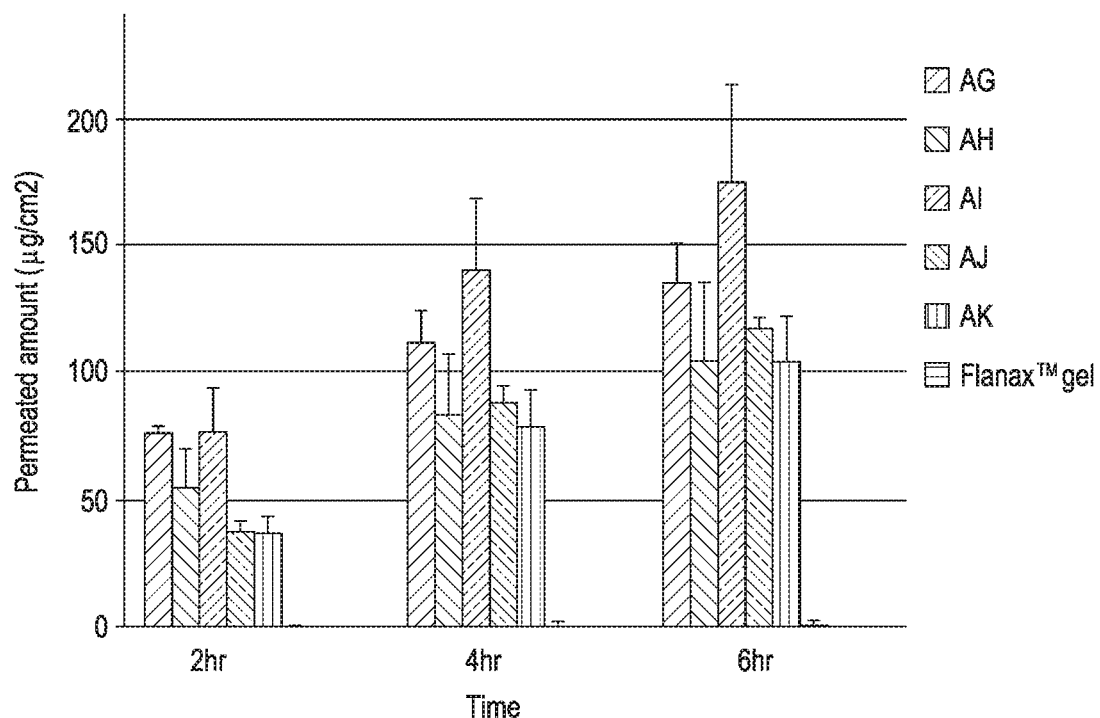
FIG. 7 is a histogram showing skin permeation of topical naproxen free acid compositions having varying amounts of lactic acid over a six-hour time period.

The effect of lactic acid on skin permeation performance of naproxen compositions is illustrated in Tables 13-16, below, and in FIGS. 6 and 7.

TABLE 13

Naproxen Salt Compositions With Varying Amounts of Lactic Acid

| | AB | AC | AD | AE | AF | Flanax™ |
|---|---|---|---|---|---|---|
| Naproxen Na | 1.5 | 1.5 | 1.5 | 1.5 | 1.5 | 5.5 |
| Propylene glycol | 10 | 10 | 10 | 10 | 10 | |
| Lauryl lactate | 3 | 3 | 3 | 3 | 3 | |
| Lactic acid | 1.5 | 2.5 | 0.5 | 0 | 0 | |
| Cationic guar gum[11] | 2 | 2 | 2 | 2 | 2 | |
| Glycerol monolaurate | 3 | 3 | 3 | 3 | 3 | |
| Ethanol | 44 | 43 | 45 | 45.5 | 45.5 | |
| Water | 35 | 35 | 35 | 35 | | |
| Buffer, pH 4.5 | | | | | 35 | |
| TOTAL | 100 | 100 | 100 | 100 | 100 | |

[11]Jaguar C162; CAS No. 71329-50-5; contains 11.5% w/w water

TABLE 14

Skin Permeation Data for Naproxen Salt
Compositions With and Without Lactic Acid Cumulative Permeated Amount, $\mu g/cm^2$

| Time, hrs. | AB Amt. | ±SD | AC Amt. | ±SD | AD Amt. | ±SD | AE Amt. | ±SD | AF Amt. | ±SD | Flanax™ Amt. | ±SD |
|---|---|---|---|---|---|---|---|---|---|---|---|---|
| 2 | 59.4 | 24.7 | 79.3 | 3.6 | 52.3 | 10.0 | 20.8 | 6.8 | 13.0 | 0.0 | 0.2 | 0.4 |
| 4 | 109.7 | 35.1 | 161.8 | 33.9 | 113.8 | 25.9 | 56.4 | 15.4 | 35.5 | 0.0 | 0.7 | 1.2 |
| 6 | 142.0 | 40.5 | 200.4 | 47.2 | 164.2 | 37.4 | 93.4 | 28.9 | 52.5 | 2.4 | 1.0 | 1.7 |

The results shown in Table 13 indicate that elimination of lactic acid resulted in reduced skin permeation of the composition.

TABLE 15

Naproxen Free Acid Compositions
With Varying Amounts of Lactic Acid

| | AG | AH | AI | AJ | AK | Flanax™ |
|---|---|---|---|---|---|---|
| Naproxen Na | | | | | | 5.5 |
| Naproxen | 1.5 | 1.5 | 1.5 | 1.5 | 1.5 | |
| Propylene glycol | 10 | 10 | 10 | 10 | 10 | |
| Lauryl lactate | 3 | 3 | 3 | 3 | 3 | |
| Lactic acid | 1.5 | 2.5 | 0.5 | 0 | 0 | |
| Cationic guar gum[12] | 2 | 2 | 2 | 2 | 2 | |
| Glycerol monolaurate | 3 | 3 | 3 | 3 | 3 | |
| Ethanol | 44 | 43 | 45 | 45.5 | 45.5 | |
| Water | 35 | 35 | 35 | 35 | 0 | |
| Buffer, pH 4.5 | | | | | 35 | |
| TOTAL | 100 | 100 | 100 | 100 | 100 | |

[12]Jaguar C162; CAS No. 71329-50-5; contains 11.5% w/w water

The compositions shown in Table 15 were applied to cadaver skin from the back of a 65-year old male, weighing 150 pounds, in a Franz cell skin permeation study. The results are shown in Table 16, below.

TABLE 16

Skin Permeation Data for Naproxen Free Acid
Compositions With Varying Amounts of Lactic Acid

| Time, | AG | | AH | | AI | | AJ | | AK | | Flanax ™ | |
|---|---|---|---|---|---|---|---|---|---|---|---|---|
| | Cumulative Permeated Amount, µg/cm$^2$ | | | | | | | | | | | |
| hrs. | Amt. | ±SD | Amt. | ±SD | Amt. | ±SD | Amt. | ±SD | Amt. | ±SD | Amt. | ±SD |
| 2 | 77.2 | 2.1 | 55.3 | 15.3 | 77.2 | 17.3 | 38.4 | 3.4 | 37.7 | 6.1 | 0.2 | 0.4 |
| 4 | 112.5 | 12.9 | 83.6 | 24.0 | 141.1 | 27.9 | 88.6 | 6.6 | 79.3 | 14.5 | 0.7 | 1.2 |
| 6 | 135.9 | 14.9 | 105.7 | 30.0 | 175.4 | 38.8 | 118.0 | 3.4 | 105.1 | 17.0 | 1.0 | 1.7 |

The data in Table 16 indicate that omission of lactic acid from the composition reduces skin permeation.

Oxybenzone was added to naproxen containing compositions as a photostabilizer, and skin permeation performance of these compositions was evaluated.

TABLE 17

Naproxen Compositions With Photostabilizer

| | AL | AM | AN | AO | Flanax ™ |
|---|---|---|---|---|---|
| Naproxen Na | 1.5 | | 1.5 | | 5.5 |
| Naproxen | | 1.5 | | 1.5 | |
| Propylene glycol | 10 | 10 | 10 | 10 | |
| Lauryl lactate | 3 | 3 | 3 | 3 | |
| Lactic acid | 1.5 | 1.5 | 1.5 | 1.5 | |
| Cationic guar gum[13] | 2 | 2 | 2 | 2 | |
| Oxybenzone | | | 1.5 | 1.5 | |
| Glycerol monolaurate | 3 | 3 | 3 | 3 | |
| Ethanol | 44 | 44 | 42.5 | 42.5 | |
| Water | 35 | 35 | 35 | 35 | |
| TOTAL | 100 | 100 | 100 | 100 | |

[13] Jaguar C162; CAS No. 71329-50-5; contains 11.5% w/w water

Figure 8:
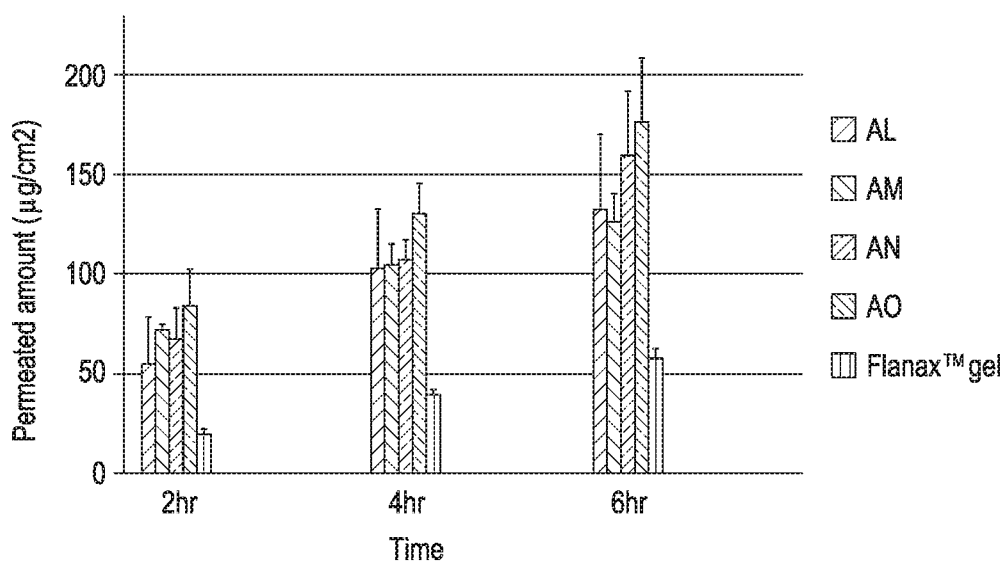
FIG. 8 is a histogram showing skin permeation of naproxen in topical compositions containing a photostabilizer.

The compositions shown in Table 17 were applied to cadaver skin from the back of a 67-year old male, weighing 150 pounds, in a Franz cell skin permeation study. The results are shown in Table 18, below, and in FIG. 8.

TABLE 18

Skin Permeation Data for Naproxen
Compositions Containing a Photostabilizer

| Time, | AL | | AM | | AN | | AO | | Flanax ™ | |
|---|---|---|---|---|---|---|---|---|---|---|
| | Cumulative Permeated Amount, µg/cm$^2$ | | | | | | | | | |
| hrs. | Amt. | ±SD | Amt. | ±SD | Amt. | ±SD | Amt. | ±SD | Amt. | ±SD |
| 2 | 55.38 | 23.00 | 72.03 | 1.97 | 67.64 | 15.52 | 84.38 | 18.27 | 19.78 | 0.24 |
| 4 | 102.31 | 32.72 | 104.91 | 12.05 | 107.28 | 11.96 | 129.91 | 16.31 | 39.61 | 2.57 |
| 6 | 132.43 | 37.79 | 126.72 | 13.89 | 160.08 | 31.87 | 177.37 | 31.58 | 58.57 | 4.48 |

Data in Table 18 indicate that the presence of a photostabilizer does not materially affect the skin permeation of the naproxen compositions.

Oxybenzone was added to diclofenac-containing compositions as a photostabilizer, and skin permeation performance of these compositions was evaluated.

TABLE 19

Diclofenac Compositions With Photostabilizer

|  | AP | AQ | Voltaren ™ |
|---|---|---|---|
| Diclofenac Na |  |  | 1 |
| Diclofenac diethylamine | 0.75 | 0.75 |  |
| Propylene glycol | 10 | 10 |  |
| Lauryl lactate | 3 | 3 |  |
| Lactic acid | 1.5 | 1.5 |  |
| Cationic guar gum[14] | 2 | 2 |  |
| Oxybenzone |  | 0.75 |  |
| Glycerol monolaurate | 3 | 3 |  |
| Ethanol | 39.75 | 39.75 |  |
| Water | 40 | 39.25 |  |
| TOTAL | 100 | 100 |  |

[14]Jaguar C162; CAS No. 71329-50-5; contains 11.5% w/w water

Figure 9:
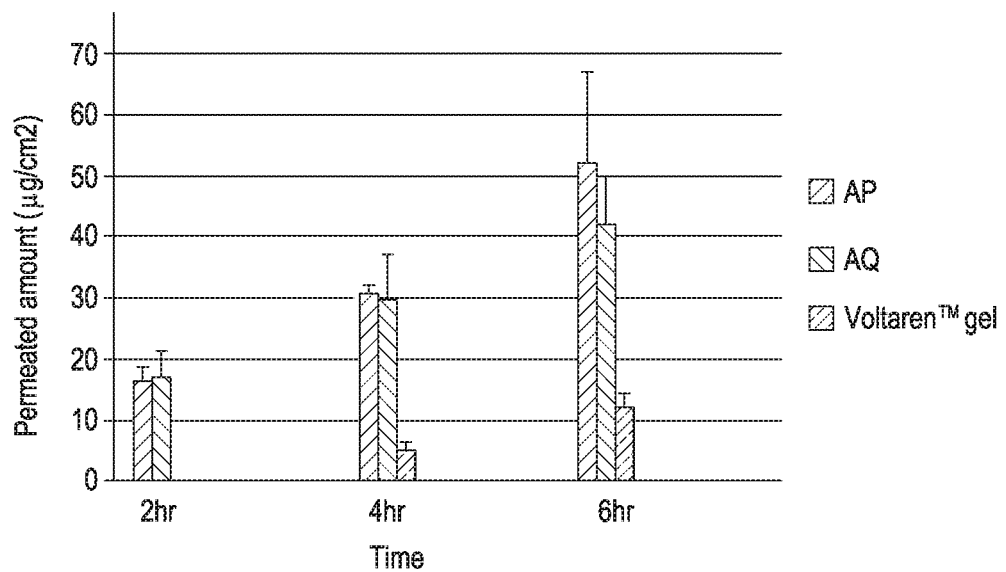
FIG. 9 is a histogram showing skin permeation of diclofenac in topical compositions containing a photostabilizer.

The compositions shown in Table 19, above, were applied to cadaver skin from the thigh of a 72-year old female, weighing 108 pounds, in a Franz cell skin permeation study. The results are shown in Table 20, below, and in FIG. 9.

TABLE 20

Skin Permeation Data for Diclofenac Compositions Containing a Photostabilizer

| | Cumulative Permeated Amount, µg/cm² | | | | | |
|---|---|---|---|---|---|---|
| Time, | AP | | AQ | | Voltaren ™ | |
| hrs. | Amt. | ±SD | Amt. | ±SD | Amt. | ±SD |
| 2 | 16.52 | 2.13 | 17.01 | 4.27 | 0.00 | 0.00 |
| 4 | 30.99 | 0.99 | 29.82 | 7.47 | 5.44 | 1.37 |
| 6 | 52.26 | 14.64 | 42.24 | 7.78 | 12.49 | 1.88 |

Data in Table 20 indicate that the presence of a photostabilizer does not materially affect the skin permeation of the diclofenac compositions.

The stability and photostability of the prepared diclofenac containing compositions was evaluated at 25° C. and after 5-minute UV light exposure using a Fusion UV system with F6005 bulb at 240 watts/cm. The results are shown in Table 21, below.

TABLE 21

Diclofenac Compositions - Stability Study

| | Diclofenac Diethylamine Recovered | | Oxybenzone Recovered | |
|---|---|---|---|---|
| Composition | wt.-% | ±SD | wt.-% | ±SD |
| STABILITY @ 25° C. | | | | |
| AP | 99.7 | 0.94 | N/A | N/A |
| AQ | 105.0 | 0.10 | 109.8 | 0.70 |
| PHOTOSTABILITY @ 25° C. | | | | |
| AP | 65.8 | 0.11 | N/A | N/A |
| AQ | 93.5 | 0.65 | 107.8 | 0.60 |

The data in Table 21, above, demonstrate that oxybenzone enhances the photostability of diclofenac-containing compositions.

Oxybenzone was added to ibuprofen-containing compositions as a photostabilizer, and skin permeation performance of these compositions was evaluated. The compositions are shown in Table 22, below.

TABLE 22

Ibuprofen Compositions With Photostabilizer

|  | AR | AS | Ibutop ™ |
|---|---|---|---|
| Ibuprofen | 5 | 5 | 5 |
| Propylene glycol | 10 | 10 |  |
| Oxybenzone |  | 5 |  |
| Lauryl lactate | 3 | 3 |  |
| Lactic acid | 1.5 | 1.5 |  |
| Cationic guar gum[15] | 2 | 2 |  |
| Glycerol monolaurate | 3 | 3 |  |
| Ethanol | 35.5 | 35.5 |  |
| Water | 40 | 35 |  |
| TOTAL | 100 | 100 |  |

[15]Jaguar C162; CAS No. 71329-50-5; contains 11.5% w/w water

The compositions shown in Table 22, above, were applied to cadaver skin from the thigh of a 61-year old male, weighing 170 pounds, in a Franz cell skin permeation study. The observed results are shown in Table 23, below.

TABLE 23

Skin Permeation Data for Ibuprofen Compositions Containing a Photostabilizer

| | Cumulative Permeated Amount, µg/cm² | | | | | |
|---|---|---|---|---|---|---|
| Time, | AR | | AS | | Ibutop ™ | |
| hrs. | Amt. | ±SD | Amt. | ±SD | Amt. | ±SD |
| 2 | 34.49 | 5.51 | 20.70 | 4.77 | 4.04 | 2.91 |
| 4 | 92.21 | 6.72 | 57.17 | 9.03 | 28.20 | 3.67 |
| 6 | 134.06 | 27.44 | 123.17 | 21.27 | 53.55 | 9.94 |

The stability and photostability of the prepared ibuprofen compositions shown in Table 22, above, was evaluated at 25° C. and after a 10-minute UV light exposure using a Fusion UV system with F6005 bulb at 240 watts/cm. The results are shown in Table 24, below.

TABLE 24

Ibuprofen Compositions - Stability Study

| | Ibuprofen Recovered | | Oxybenzone Recovered | |
|---|---|---|---|---|
| Composition | wt.-% | ±SD | wt.-% | ±SD |
| STABILITY @ 25° C. | | | | |
| AR | 103.6 | 1.92 | N/A | N/A |
| AS | 104.4 | 2.71 | 101.0 | 2.32 |
| PHOTOSTABILITY @ 25° C. | | | | |
| AR | 87.5 | 0.75 | N/A | N/A |
| AS | 99.1 | 0.35 | 104.1 | 0.35 |

Topical compositions containing diclofenac and oxybenzone shown in Table 25, below, were prepared for stability testing.

TABLE 25

Topical Diclofenac Compositions with Oxybenzone

|  | AT | AU | AV |
|---|---|---|---|
| Diclofenac | 1 | 1 | 1 |
| Propylene glycol | 5 | 0 | 5 |
| Lauryl lactate | 3 | 3 | 3 |
| Hexylene glycol |  |  | 5 |
| Lactic acid | 1.5 | 1.5 | 1.5 |
| 2-(Ethoxyethoxy)ethanol | 5 | 10 | 5 |
| Cationic guar gum[16] | 2 | 2 | 2 |
| Poloxamer | 0.5 | 0.5 | 0.5 |
| Oxybenzone | 1.5 | 1.5 | 1.5 |
| Glycerol monolaurate | 1 | 1 | 1 |
| Ethanol | 43.5 | 43.5 | 38.5 |
| Water | 35 | 35 | 35 |
| Dipropylene glycol dibenzoate | 1 | 1 | 1 |
| TOTAL | 100 | 100 | 100 |

[16]Jaguar C162; CAS No. 71329-50-5; contains 11.5% w/w water

The prepared compositions were transparent gels, and were evaluated for stability at 25° C. with and without 5-minute UV light exposure using a Fusion UV system with F6005 bulb at 240 watts/cm. The results are shown in Table 26, below.

TABLE 26

Diclofenac Compositions - Stability Study

|  | Diclofenac Recovered |  | Oxybenzone Recovered |  |
|---|---|---|---|---|
| Composition | wt.-% | ±SD | wt.-% | ±SD |
| STABILITY @ 25° C. | | | | |
| AT | 102.91 | 0.37 | 102.73 | 0.83 |
| AU | 102.48 | 0.29 | 103.03 | 0.50 |
| AV | 103.07 | 0.26 | 103.28 | 0.65 |
| PHOTOSTABILITY @ 25° C. | | | | |
| AT | 90.91 | 0.64 | 102.72 | 0.27 |
| AU | 90.06 | 0.40 | 103.46 | 0.89 |
| AV | 91.01 | 0.19 | 102.87 | 0.21 |

Topical compositions containing naproxen and naproxen sodium shown in Table 27, below, were prepared for stability testing.

TABLE 27

Topical Naproxen and Naproxen Sodium Compositions with Oxybenzone

|  | AW | AX | AY |
|---|---|---|---|
| Naproxen Na | 1.5 |  | 1.5 |
| Naproxen |  | 1.5 |  |
| Oxybenzone | 1.5 | 1.5 | 1.5 |
| Propylene glycol | 10 | 10 | 10 |
| Lauryl lactate | 3 | 3 | 3 |
| Lactic acid | 1.5 | 1.5 | 1.5 |
| Cationic guar gum[17] | 2 | 2 | 2 |
| Glycerol monolaurate | 1 | 1 | 1 |
| Ethanol | 44 | 44 | 43 |
| Water | 35 | 35 | 35 |
| Poloxamer | 0.5 | 0.5 | 0.5 |
| Dipropylene glycol dibenzoate |  |  | 1 |
| TOTAL | 100 | 100 | 100 |

[17]Jaguar C162; CAS No. 71329-50-5; contains 11.5% w/w water

TABLE 28

Naproxen Compositions - Stability Study

|  | Naproxen Recovered |  | Oxybenzone Recovered |  |
|---|---|---|---|---|
| Composition | wt.-% | ±SD | wt.-% | ±SD |
| STABILITY @ 25° C. | | | | |
| AW | 102.9 | 0.19 | 102.9 | 0.45 |
| AX | 102.9 | 0.23 | 103.3 | 0.44 |
| AY | 99.3 | 1.02 | 105.9 | 1.27 |
| PHOTOSTABILITY @ 25° C. | | | | |
| AW | 99.6 | 1.08 | 101.3 | 0.95 |
| AX | 99.9 | 0.29 | 101.2 | 0.31 |
| AY | 99.1 | 0.27 | 103.9 | 0.13 |

Sulisobenzone was added to ibuprofen-containing topical compositions as photostabilizer, and skin permeation performance of those topical compositions was evaluated. The compositions are shown in Table 29, below.

TABLE 29

Ibuprofen Compositions with Sulisobenzone

|  | AZ | BA | BB | BC |
|---|---|---|---|---|
| Ibuprofen | 5 | 5 | 5 | 5 |
| Propylene glycol | 0 | 5 | 2.5 | 2.5 |
| Oxybenzone | 2.5 | 0 | 0 | 2.5 |
| Lauryl lactate | 3 | 3 | 3 | 3 |
| Hexylene glycol | 0 | 0 | 2.5 | 2.5 |
| Lactic acid | 1.5 | 1.5 | 1.5 | 0 |
| Sulisobenzone | 5 | 5 | 5 | 2.5 |
| Cationic guar gum[18] | 2 | 2 | 2 | 2 |
| Poloxamer | 0.5 | 0.5 | 0.5 | 0.5 |
| 2-(Ethoxyethoxy)ethanol | 10 | 10 | 10 | 10 |
| Glycerol monolaurate | 1 | 1 | 1 | 1 |
| Ethanol | 39.5 | 32 | 32 | 33.5 |
| Water | 35 | 35 | 35 | 35 |
| TOTAL | 100 | 100 | 100 | 100 |

[18]Jaguar C162; CAS No. 71329-50-5; contains 11.5% w/w water

Compositions AZ, BA and BB shown in Table 29, above, were applied to cadaver skin from the thigh of a 61-year old male, weighing 170 pounds, in a Franz cell skin permeation study. The observed results are shown in Table 30, below.

TABLE 30

Skin Permeation Data for Ibuprofen Compositions Containing Sulisobenzone

| | Cumulative Permeated Amount, μg/cm² | | | | | | | |
|---|---|---|---|---|---|---|---|---|
| Time, | AZ | | BA | | BB | | Ibutop ™ | |
| hrs. | Amt. | ±SD | Amt. | ±SD | Amt. | ±SD | Amt. | ±SD |
| 2 | 29.65 | 4.24 | 24.08 | 15.77 | 28.19 | 5.44 | 9.22 | 0.43 |
| 4 | 67.25 | 5.72 | 73.08 | 6.70 | 59.00 | 14.04 | 26.56 | 2.68 |
| 6 | 89.93 | 15.32 | 106.11 | 25.25 | 81.68 | 4.52 | 43.37 | 1.67 |

The stability and photostability of the prepared ibuprofen compositions shown in Table 29, above, was evaluated at 25° C. and after a 5-minute UV light exposure using a Fusion UV system with F6005 bulb at 240 watts/cm. The results are shown in Table 31, below.

TABLE 31

Ibuprofen Compositions - Stability Study

| Composition | Ibuprofen Recovered | | Oxybenzone Recovered | | Sulisobenzone Recovered | |
|---|---|---|---|---|---|---|
| | wt.-% | ±SD | wt.-% | ±SD | wt.-% | ±SD |
| STABILITY @ 25° C. | | | | | | |
| AZ | 100.1 | 0.45 | 103.9 | 0.44 | N/A | N/A |
| BA | 77.3 | 1.62 | N/A | N/A | 106.00 | 2.16 |
| BB | 78.5 | 1.21 | N/A | N/A | 105.20 | 1.97 |
| BC | 89 | 1.04 | 108.6 | 1.54 | 102.40 | 1.13 |
| PHOTOSTABILITY @ 25° C. | | | | | | |
| AZ | 97.69 | 0.83 | 103.29 | 0.98 | N/A | N/A |
| BA | 72.2 | 0.96 | N/A | N/A | 105.5 | 1.61 |
| BB | 73.9 | 0.37 | N/A | N/A | 105.1 | 0.80 |
| BC | 85.5 | 0.25 | 109.6 | 1.16 | 103.4 | 0.57 |

The invention claimed is:

1. An aqueous, topical anti-inflammatory gel composition having a pH value in the range of about 3 to about 5.5, which comprises: a non-steroidal anti-inflammatory drug (NSAID) which is an arylalkanoic acid, a lactate ester of a C2 to C16 saturated aliphatic alcohol, a monoprotic organic acid having a pKa value in the range of about 3.8 to about 5, a C2 to C8 saturated aliphatic alcohol, a monoglyceride solubility enhancer, and a cationic guar gum;
  wherein lactate ester of a C2 to C16 saturated aliphatic alcohol is Lauryl lactate and the a C2 to C8 saturated aliphatic alcohol is a monohydric alcohol;
  wherein the arylalkanoic acid is present in an amount in the range of about 0.5 to about 7 percent by weight of the composition; and the cationic guar gum is present in an amount in the range of about 1 to about 5 percent by weight of the composition.

2. The anti-inflammatory composition in accordance with claim 1 wherein the arylalkanoic acid is an arylethanoic acid.

3. The anti-inflammatory composition in accordance with claim 2 wherein the arylethanoic acid is diclofenac.

4. The anti-inflammatory composition in accordance with claim 2 wherein the arylethanoic acid is diclofenac sodium.

5. The anti-inflammatory composition in accordance with claim 2 wherein the arylethanoic acid is diclofenac diethylamine.

6. The anti-inflammatory composition in accordance with claim 1 wherein the arylalkanoic acid is an arylpropanoic acid.

7. The anti-inflammatory composition in accordance with claim 6 wherein the arylpropanoic acid is naproxen.

8. The anti-inflammatory composition in accordance with claim 6 wherein the arylpropanoic acid is naproxen sodium.

9. The anti-inflammatory composition in accordance with claim 6 wherein the arylpropanoic acid is ibuprofen.

10. The anti-inflammatory composition in accordance with claim 6 wherein the arylpropanoic acid is ketoprofen.

11. The anti-inflammatory composition in accordance with claim 1 wherein the monohydric alcohol is ethanol.

12. The anti-inflammatory composition in accordance with claim 1 wherein the monoprotic organic acid has a pKa value in the range of about 4.6 to about 4.8.

13. The anti-inflammatory composition in accordance with claim 1 wherein the cationic guar gum includes hydroxypropyl-trimethylammonium groups.

14. The anti-inflammatory composition in accordance with claim 13 wherein the cationic guar gum is guar, 2-hydroxy-3-(trimethylammonium) propyl ether chloride.

15. The anti-inflammatory composition in accordance with claim 1 wherein the solubility enhancer is glycerol monolaurate.

16. The anti-inflammatory composition in accordance with claim 1 further including a photostabilizer.

17. The anti-inflammatory composition in accordance with claim 16 wherein the photostabilizer is sulisobenzone.

* * * * *